United States Patent
Albertini et al.

(10) Patent No.: US 6,266,994 B1
(45) Date of Patent: Jul. 31, 2001

(54) METHOD AND APPARATUS FOR MEASURING PROPERTIES OF MATERIALS OR STRUCTURES

(75) Inventors: Carlo Albertini, Ispra (IT); Mikhail Mogilevsky, Novosibirsk (RU)

(73) Assignee: European Atomic Energy Community, Luxembourg ( * ) Notice: Subject to any disclaimer, the term of this patent is extended or adjusted under 35 U.S.C. 154(b) by 0 days.

(21) Appl. No.: 09/355,255

(22) PCT Filed: Sep. 26, 1997

(86) PCT No.: PCT/EP97/05434
§ 371 Date: Sep. 16, 1999
§ 102(e) Date: Sep. 16, 1999

(87) PCT Pub. No.: WO98/33053
PCT Pub. Date: Jul. 30, 1998

(30) Foreign Application Priority Data

Jan. 24, 1997 (EP) .................................. 97300469

(51) Int. Cl.⁷ .................................................. G01M 7/00
(52) U.S. Cl. .............................................. 73/12.01; 73/598
(58) Field of Search .................... 73/597, 598, 12.01, 73/841, 844

(56) References Cited

U.S. PATENT DOCUMENTS 4,379,401 * 4/1983 Miguel ................................ 73/12.08
5,487,298 * 1/1996 Davis et al. ........................ 73/12.05
6,023,976 * 2/2000 Borza et al. ............................ 73/598

OTHER PUBLICATIONS

Albertini et al., "Study of the true tensile stress–strain diagram of plain concrete with real size aggregate: need for and design of a large Hopkinson bar bundle" Journal De Physique IV, vol. 4, Sep.*

* cited by examiner

*Primary Examiner*—Max Noori
(74) *Attorney, Agent, or Firm*—Welsh & Katz, Ltd.

(57) ABSTRACT

Stress wave measuring apparatus includes a Hopkinson bar or pressure bar bundle system comprising an input bar bundle having input bars, and an output bar bundle having output bars 104a. A brittle test specimen is positioned in between the input and output bar bundles. Means is provided to induce a one dimensional compression force into the bar bundles. Instrumentation is introduced onto the input and output bars for measuring values of shear wave or crack propagation. The specimen may be placed under different stress conditions measured by appropriate instrumentation on the bar bundles. In one embodiment, a rod gauge is glued to a rock massive and arranged to measure wave effects generated in the rock massive. Other arrangements provide amplification of the wave effects prior to measurement by instrumentation on the gauge 500.

22 Claims, 5 Drawing Sheets

METHOD AND APPARATUS FOR MEASURING PROPERTIES OF MATERIALS OR STRUCTURES

This invention relates to improvements in or relating to measuring properties of materials or structures and is more particularly but not exclusively concerned with measuring the mechanical properties of brittle construction materials or the mechanical properties of brittle geological structures. An exclusive performance of some improvements as described herein is that of measuring the mechanical properties under dynamic and quasi-static loading of a material specimen both as a global value and as value distribution over the specimen cross section.

Mechanical characteristics (given by stress strain curves, the influence on those curves of temperature and strain rate, fracture energy details of deformation mechanisms and so on) have been studied successfully in plastics, pure metals and alloys and the knowledge gained thereby has provided a scientific base towards optimum production and practical use of such materials. However, the situation with brittle materials or structures is much more complicated. From a practical standpoint, conventional test installations only allow the rupture limit of such materials to be measured with a corresponding large scatter or dispersion owing to the influence of surface micro-cracks induced in the material or structure under test. There is an ever increasing need to reduce the enormous losses due to earthquake and accident impact loading and thus there is a need to obtain reliable information about rupture generation and development in brittle materials of high importance such as concrete, reinforced concrete, ceramics, composites and rock materials: Here an important point is the measurement of the energy released as mechanical wave during the fracture development in the brittle construction materials or in the rock materials; when the masses and volumes of rocks are very large the energy release during fracture gives origin to seismic waves whose precise measurement remains an open problem.

It is an object of the present invention to provide apparatus (and method) for measuring properties of materials or structures more particularly during deformation and fracture which is improved in at least some respect.

According to one aspect of the present invention there is provided apparatus suitable for measuring mechanical properties of characteristics of a brittle material or structure, said apparatus comprising a Hopkinson bar or pressure bar system comprising an input bar bundle and an output bar bundle, each said bundle comprising a plurality of parallel bars each equipped with instrumentation for measuring values of longitudinal stress wave or crack propagation parameters in a brittle material specimen or structure under test located, in use, in between the input and output bar bundles.

Further according to this aspect of the present invention there is provided a method of measuring mechanical properties or characteristics of a brittle material or structure, said method comprising placing a Hopkinson bar or pressure bar system, comprising an input bar bundle and an output bar bundle, under load, and thus placing a brittle material specimen or structure located, in use, in between the input and output bar bundles, under load, and measuring values of shear wave or shear crack propagation parameters in the brittle material specimen or structure from instrumentation provided on a plurality of parallel bars forming each said bar bundle.

Usually, each bar o: the bundle gives the local mechanical properties of the part of specimen cross section facing of the bar; while summing the measurements of the bars of the bundle one obtains the global mechanical properties of the material specimen or structure.

Means may be provided for placing the bar bundles and thus the material specimen or structure under test in compression in a direction along the axis of the bar bundles. In one embodiment of the apparatus each bar of the bundles is equipped with instrumentation to measure locally the stress-strain relationship of the material specimen or structure under test in addition to measuring values of absorbed energy during rupturing of the material specimen or structure under test, as well as values of shear wave propagation with a known component of compression stress in a crack plane, the orientation of a rupture surface.

In a further embodiment of the apparatus, each bar of the bundles may be equipped with means for measuring the velocity of a shear crack propagation where the material specimen or structure under test is placed in "pure shear". "Pure shear" means that there is no normal stress in the plane of shear. In this instance, the bar bundles are used in an unusual manner for a Hopkinson bar or pressure bar system in that they are used as receptors of waves emitted by propagating cracks and thus giving a measure of the energy released by crack propagation.

In a further embodiment of the apparatus, each bar bundle is arranged to measure the stress-strain relationship in the material specimen or structure under test in addition to measuring values of energy absorption during deformation of said material specimen or structure and the velocity of shear crack propagation therein in conditions of controlled "hydrostatic" pressure. The term "hydrostatic" as applied in this instance means that loading of the material specimen or structure under test is combined from equal stress-hydrostatic components plus excess load along one direction.

Although the above apparatus is suitable for measuring properties of brittle materials, it could also be used for investigating rupture processes in plastic materials at the stage of a neck development.

Additionally, means may be provided for placing the Hopkinson bar bundles and material structure under test in tension, each bar being provided with instrumentation to measure the stress strain relationship in a particular region of the material specimen or structure, values of absorbed energy during the rupture process and values of longitudinal wave propagation within the material or structure, as is already known from the Paper already presented by the inventors entitled "Study of the true tensile stress strain diagram of plain concrete with real size aggregate; need for and design of a large Hopkinson bar bundle" appearing in the Journal de Physique IV Colloque C8, supplement au Journal de Physique III, volume 4- September 1994, the entire content of which is hereby included into the present specification by reference. The aspect of the present invention as aforedescribed represents a further development over and above the arrangement shown in this paper.

The aforementioned paper only mentions placing the Hopkinson bar bundles in one dimensional tension and there is no mention of instrumentation for obtaining values of shear wave propagation or velocity measurement of shear crack propagation.

Embodiments of the present invention may provide instrumentation for measuring the following complex of deformation characteristics of brittle materials:

The stress-strain relationship and energy absorption in the material specimen or structure under test during the deformation process, including during the falling part of the load, in conditions of simple stress-state (e.g. tension or compression) and in conditions of complex stress-state (e.g. tension—tension, under hydrostatic pressure) and accurate measurements of propagation velocities of both longitudinal and shear waves in such conditions and therefore have a measure of energy release from a propagating fracture which is the basic phenomenon of an earthquake.

The Hopkinson bar system is widely used for the study of mechanical characteristics of materials in conditions of high velocity deformation (see for example the Paper by U.S. Linholm entitled "Some experiments with the split Hopkinson pressure bar, J. Mech.Phys Solids 1964 volume 12 317 to 335). The principal feature of such system is the use of two sufficiently long elastic bars (input and output bars) located on opposite sides of a sample for test and analysis of the deformation process through signals of incident, reflected and a transmitted waves.

The aforementioned Paper by the inventors appearing in the Journal de Physique IV represents a modification of the Hopkinson bar system by replacing the input and output bars by input and output bar bundles in order to analyse the rupture process developments in large blocks of brittle materials. Each bar of the bar bundle is equipped with a strain gauge so that during the process of loading a sample by a wave propagating along the system, the signals received from the bars of the bar bundles will allow rupture development to be controlled. Thus, information is received from the individual bars (prisms) in accordance with standard Hopkinson bar methodology to find the instant position of a crack (or cracks in the case of numerous centres of crack generation). However, the present invention develops the ideas suggested in this Paper by utilising a Hopkinson or pressure bar bundle system in a new or unusual way in order to evaluate shear wave or shear crack propagation in addition to evaluating other deformation characteristics. In particular this aspect is realised by using the bars of the bundles as receptors of the longitudinal and shear waves released by the fracture propagating through the material specimen or structure.

Thus the present invention may utilise wave effects arising in the deformation and fracture processes of brittle materials or structures for measuring strength parameters and such important characteristics as velocities and amplitudes of longitudinal and shear crack propagation both in quasi-static and dynamic loading. Such measurements may allow the development of a more detailed realistic model of deformation and of fracture processes in materials.

The present invention is also concerned from a second aspect with receiving and analysing information about stress re-distribution in a geological structure such as a rock massive, which may be required for predicting earthquakes and rock impacts.

There have been many proposals for measuring earthquake wave effects but in the main the devices for measurement of such wave effects in the ground belong to two classes: different kinds of pendulums and piezoelectric gauges are discussed, for example in a paper by M. Wakabayashi, Design of Earthquake-Resistant Buildings, NY McGraw-Hill 1986 page 21 to 33.

However, the possibility of using such gauges for detailed analysis of the processes involved in the active zone of stress redistribution and accumulation of energy is limited by the effects of wave reflections not being taken into account by such gauges and by the apparent insufficient sensitivity of such gauges to all types of seismic waves characteristic of an earthquake (longitudinal, shear, surface waves etc.).

U.S. Pat. No. 5,487,298 discloses a device for measuring the intensity of high amplitude strain waves caused by the impact of a projectile or the detonation of an explosive on armour plate. The device comprises a solid cylindrical bar having a pair of strain gauges located on diametrically opposite sides of the bar and connected so as to record longitudinal strain without bending strain.

Thus, according to a second aspect of the present invention there is provided measuring apparatus arranged, in use, to measure wave effects generated in a geological structure comprising a rod intended, in use, to be fixed to the surface of the structure to receive a longitudinal wave, and wherein the rod is instrumented with sets of gauges attached to the rod in different directions to allow division of information into intensities of longitudinal and shear components of arrived perturbation, to enable measurement of shear wave or shear crack propagation in said structure.

Further according to this second aspect of the present invention there is provided a method of measuring values of shear wave or shear crack propagation in a structure using measuring apparatus comprising a rod instrumented with sets of gauges attached to the rod in different directions arranged in use to measure wave effects generated in said structure.

The rod is preferably fixed, for example by glue, to the surface of the structure (for example rock massive). The longitudinal wave may be generated either artificially (for example a shock wave from an explosive charge more particularly in a mine) or generated naturally (for example from shear cracks in the regions of active geological zones, producing through the redistribution and accumulation of energy an overloaded layer structure which can cause an earthquake of a dangerous level or a phenomenon of a similar nature but on a lesser scale—the so-called "rock impact" in mines with a complex geological structure, when a wave generated from a relatively small but closely situated source can produce severe damage).

Normally, the rod gauge is instrumented to measure information regarding longitudinal waves generated in said structure.

Furthermore, the measuring instrumentation of the rod gauge may include sets of gauges (for example electrical resistance strain gauges) attached to the rod in different directions to allow division of information into intensities of longitudinal and shear components of arrived perturbation; this division of information is important for the analysis of the nature of earthquake source.

The rod gauge may, in use, be arranged to receive an amplified signal of wave effects generated in the structure. The signal may be amplified, for example, by means of a reflecting and/or refracting part of the system or arrangement.

In order to provide a reflecting system, the measuring gauge may be positioned, in use, into a tubular hole arranged centrally of a generally convex, preferably parabolic, surface cut or shaped into the structure under test.

Alternatively, a refracting amplification system may be provided preferably including a generally cone shape of material extending between one end of the rod gauge and a suitably shaped surface of the structure (which surface may be concave or convex depending whether or not the velocity of sound waves in the cone material is greater than, or less than, the velocity of sound waves in the material of the structure). The surface of the cone in contact with the shaped or cut surface of the structure under test may be concave or convex to suit.

The material cone may comprise a liquid as a refracting material inside a rubber or plastic envelope, or the like preferably with a thin wall.

In practice, whether or not the system includes means to amplify the signal in the structure under test, three measuring gauges may be positioned mutually at right angles to one another at a location under investigation in order to give complete information about a stressed state created by a wave loading.

Further advantageous features of the present invention will be apparent from the following description and drawings.

Embodiments of apparatus and method for measuring mechanical properties of brittle materials or structures or wave effects generated in a structure in accordance with the present invention will now be described, by way of example only, with reference to the accompanying much simplified diagrammatic drawings in which.

Figure 1:
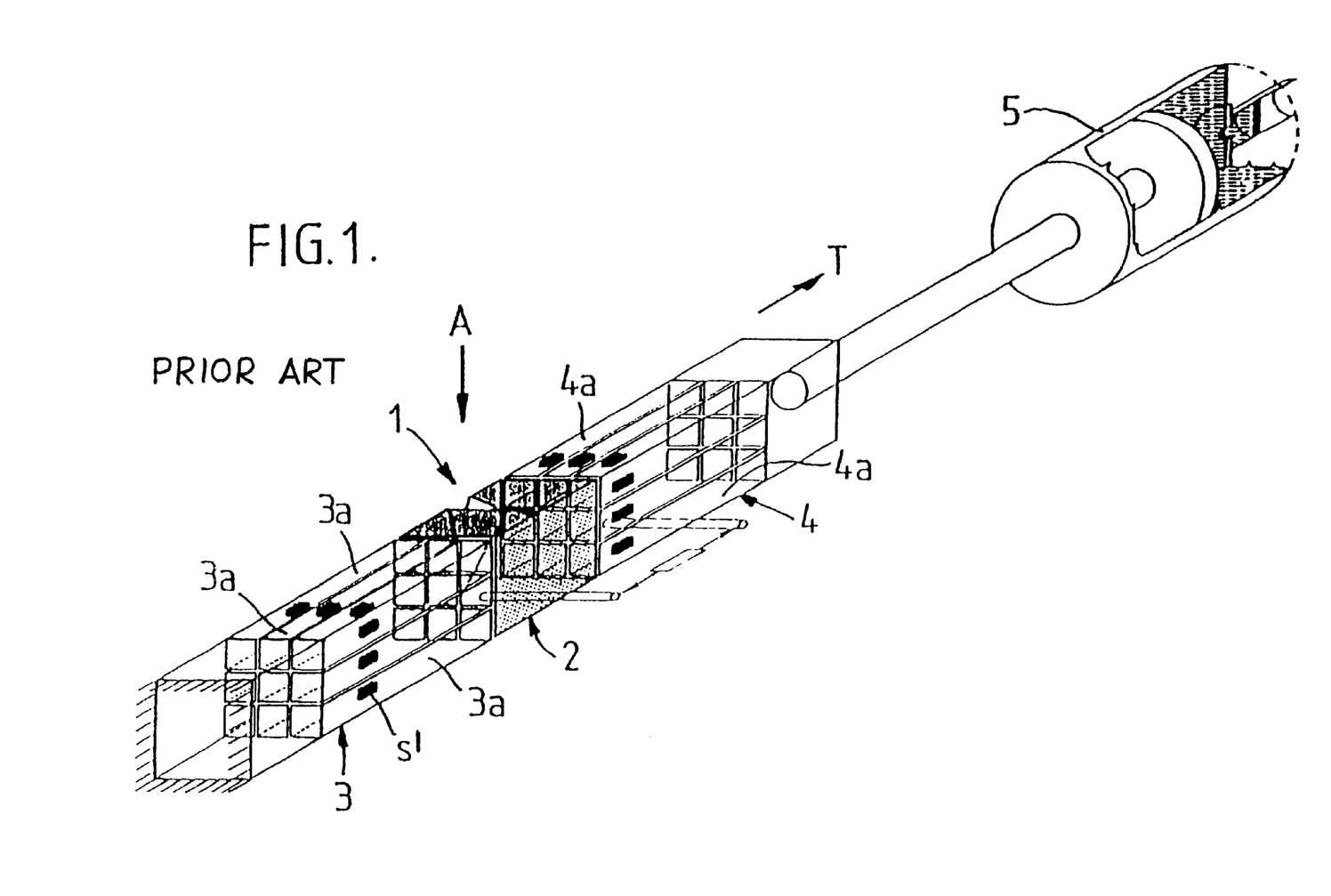
FIG. 1 shows a known Hopkinson bar bundle system for dynamic tension testing of plain concrete.

FIG. 1 of the drawings shows a known Hopkinson bar bundle system 1 arranged to test a concrete specimen 2 in a known manner. Each bar 4a of the input bar 4 and each bar 3a of the output bar 3 is equipped with measuring gauges in the form of electric resistance strain gauges s' and the concrete specimen 2 may be placed in tension by means of the hydraulic actuator 5.

Figure 2:
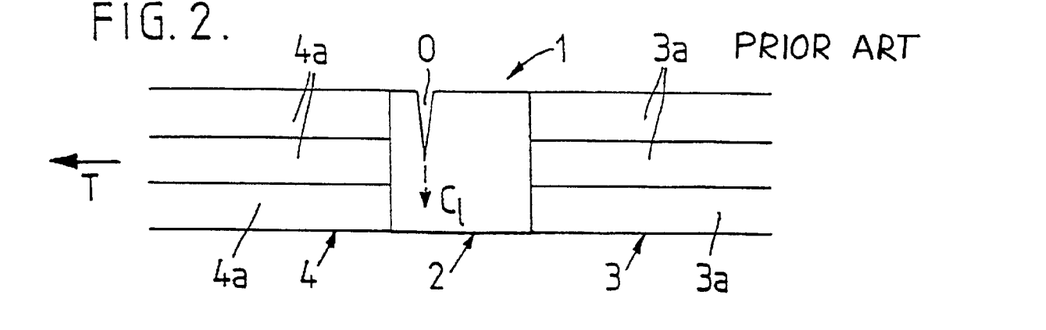
FIG. 2 shows a further simplified diagrammatic view from one side of the Hopkinson bar bundle system, for example as shown in FIG. 1, in which the Hopkinson bar bundles are placed in one dimensional tension as is known from the prior art.

FIG. 2 is a much more simplified plan view from the side of the Hopkinson bar bundles 3 and 4 (in the direction of arrow A in FIG. 1) illustrating the effect on the concrete specimen 2. Reference $C_1$ represents the velocity of a longitudinal crack propagation (longitudinal crack development occurs when the opposite sides of the concrete specimen are pulled apart in a direction perpendicular to the rupture plane to form an opening "O" more particularly as shown in FIG. 2). The one dimensional tensional force applied to the bar bundles 3 and 4 is represented by the arrow T.

The afore-described arrangement is known and the stress-strain relationship in the concrete specimen is determined by means of the bars 3a,4a individually instrumented with strain gauges s' which measure the incident, reflected and transmitted pulses concerning only the portion of the concrete specimen cross section facing the cross section of the pair of bars of the bundle. Thus, a value of absorbed energy can be obtained and a value of longitudinal wave propagation.

This technique is explained fully in the aforementioned paper of the inventors and thus need not be described in further detail.

Figure 3:
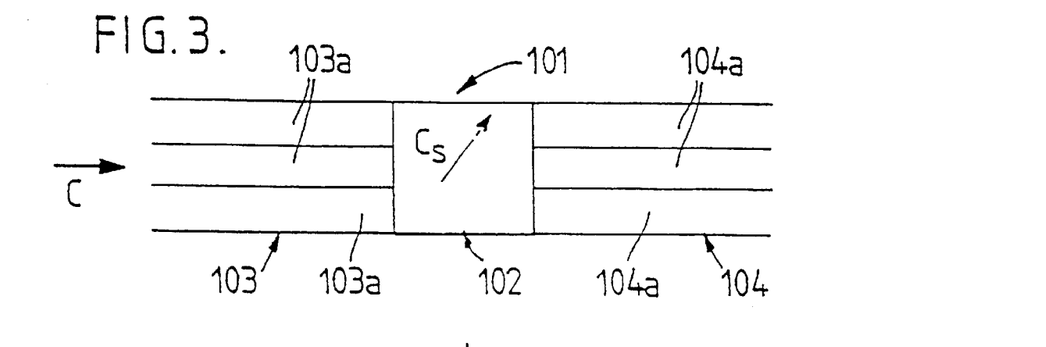
FIG. 3 shows in accordance with a first embodiment of the present invention a view similar to FIG. 2 in which the Hopkinson bars and the material under test is placed in one dimensional compression in order to generate a shear wave with a known component of compressive stress in a crack plane.

FIG. 3 is a simplified view of similar form to FIG. 2 of a Hopkinson bar or pressure bar bundle system 101 comprising an input bar bundle 103 having input bars 103a and an output bar bundle 104 having output bars 104a of a similar nature to the Hopkinson bar system. 1 shown in FIG. 1. However, instead of the Hopkinson bar bundle system 101 being equipped with a hydraulic actuator 5 to introduce a tensional force T into the Hopkinson bar system, the actuator 5 is replaced by means to induce a one dimensional quasi-static or impact compression force C into the Hopkinson bar bundles. Additionally, further instrumentation (not depicted) is introduced onto the bars 103a and 104a thus allowing a determination of a value of absorbed energy in the specimen 102 under test during the rupture process and the value of shear wave propagation with a known component of compressive stress in a crack plane, the orientation of the rupture surface. The velocity of a shear wave $C_s$ is marked on FIG. 3.

For the manner in which the specimen 102 and Hopkinson bar bundles 103 and 104 can be placed into impact compression see, for example, European Patent Applications EPA-848241, EP-A-849583 and EPA-848264.

Figure 4:
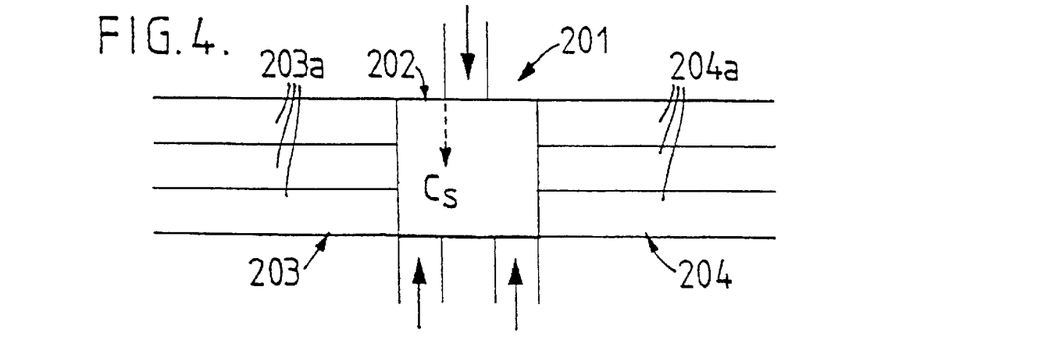
FIG. 4 shows a view, in accordance with the present invention, similar to FIG. 3 in which the material under test is placed in a condition of pure shear.

FIG. 4 shows a different scenario for measuring the velocity of shear crack propagation in a modified Hopkinson bar bundle installation 201 for a pure shear. Pure shear means that there is no normal stress in the plane of shear. $C_s$ represents the velocity of a shear wave in the specimen 202 under test. Here, the bar bundles 203 and 204 are used in an unusual way for a Hopkinson bar system since they are receptors of waves emitted by propagating cracks in the test specimen and appropriate instrumentation (not depicted) is provided on the bars 203a,204a to measure the velocity of the shear crack propagation.

Figure 5:
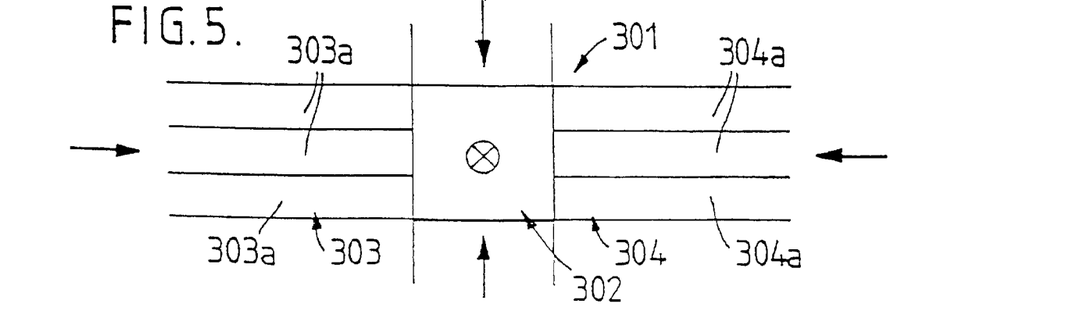
FIG. 5 shows, in accordance with the present invention, a view similar to FIG. 4 in which the material under test is placed in one dimensional compression in conditions of controlled hydrostatic pressure.

FIG. 5 shows a Hopkinson bar bundle system 301 arranged to measure the stress strain relationship in a specimen under test 302 and the value of energy absorption during all the deformation processes and velocity of shear crack propagation in conditions of controlled hydrostatic pressure. Hydrostatic pressure means that loading is combined from equal stress hydrostatic components and excess load along one direction. With bars 303a and 304a produced from high strength steel it is possible to reach a level of hydrostatic pressure of about 1 to 2 Gpa which is of a reasonable geological level.

Whilst it is envisaged that the specimens 102,202 and 302 under test are of a brittle material, the Hopkinson bar bundle systems 101,201 and 301 could alternatively be used for investigating rupture processes in plastic materials at the stage of a neck development.

Thus, each bar bundle 103,104,203,204,303,304 comprises a plurality of parallel bars 103a,104a,203a,204a, 303a,304a equipped with instrumentation for measuring values of shear wave or shear crack propagation in a brittle material 102,202,302 under test located, in use, in between the input and output bar bundles 103,104;203,204; 303,304.

Additionally, of course, any of the Hopkinson bar systems 101,102,103 could be arranged to place the specimen under test in tension as in the prior art arrangement (FIGS. 1 and 2).

Thus, the present invention may facilitate an advanced study of the deformation process in brittle materials using the basis of wave mechanics principles. The aforedescribed Hopkinson bar bundle systems 101,201,301 may enable an assimilation of a complex of essential deformation characteristics of brittle materials, such as force-displacement relationships, including the falling part of the load, value of absorbed energy, values of velocity of longitudinal and shear waves, at different stress rates and therefore of energy release as stress waves during fracture propagation and both in quasistatic and dynamic loading, allowing the development of a detailed realistic model of fracture processes and materials.

Figure 6:
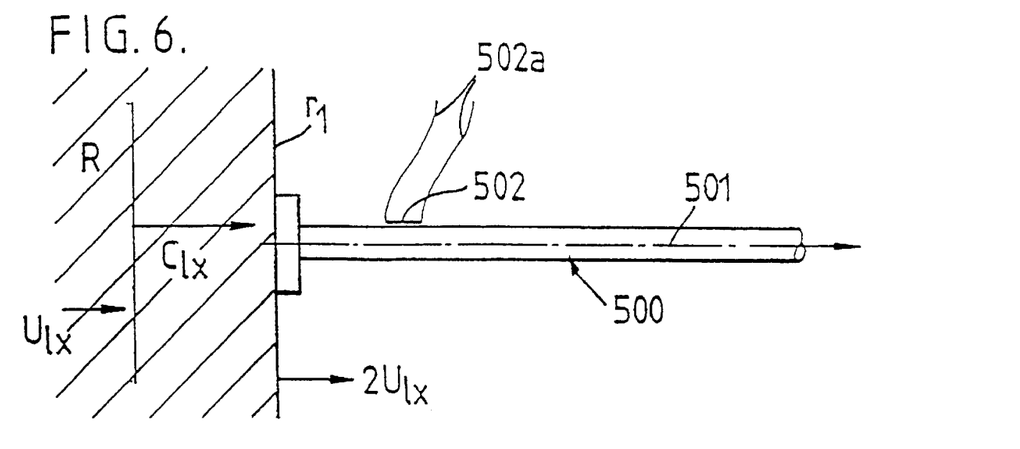
FIG. 6 shows an embodiment of a rod measuring gauge in accordance with the present invention arranged to measure particular wave effects generated in a rock massive.

FIG. 6 shows a simple rod gauge 500 which is connected, for example by gluing, to the surface $r_1$ of a rock massive R with the axis 501 of the rod measuring gauge extending normal to the surface $r_1$, said gauge being arranged to measure wave effects generated in the rock massive. The gauge 500 is arranged so that it will receive, from the longitudinal wave, falling at the surface $r_1$ with a particle velocity $U_{lx}$, a signal corresponding to the double particle velocity $2 U_{lx}$ due to the wave mechanics rule for reflection from a free surface. $C_{lx}$ indicates the velocity of the longitudinal wave. $U_{lx}$ represents the corresponding particle velocity beyond the front of the longitudinal wave. The rod 500 may be provided with measuring instrumentation 502 connected by leads 502a to analysing equipment (not shown) to measure parameters relating to the longitudinal wave.

Figure 7:
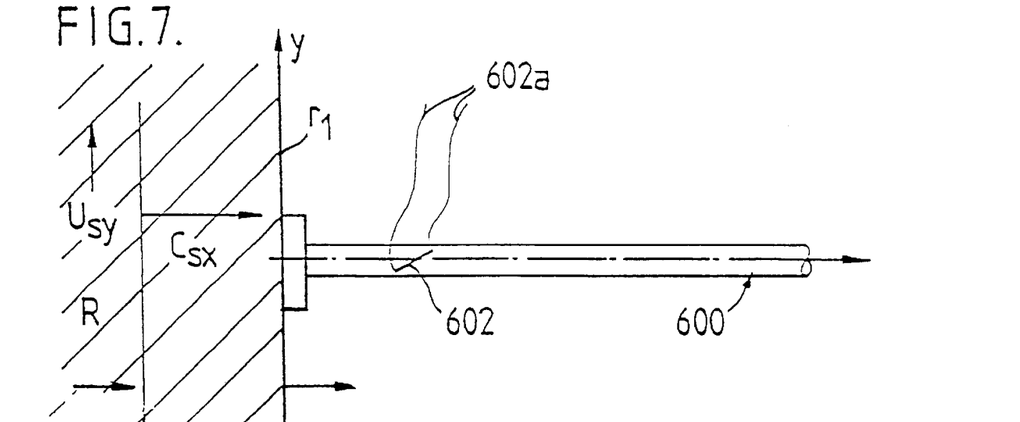
FIGS. 7 and 8 show the same rod gauge arranged to measure different wave effects generated in the rock massive.
Figure 8:
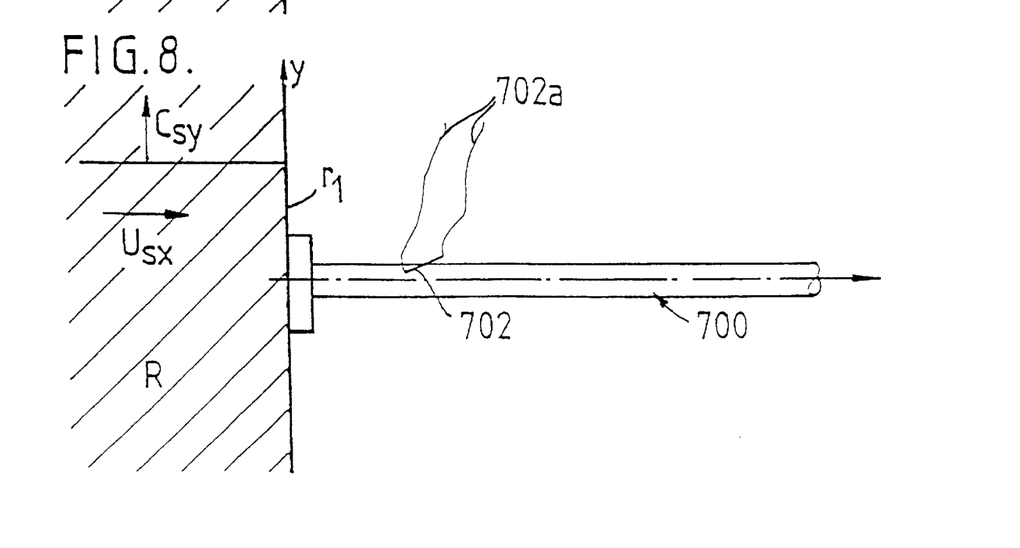

Similarly, FIGS. 7 and 8 show rod gauges 600 and 700 glued to the surface $r_1$ of the rock massive R, provided with measuring instrumentation 602,702 with leads 602a,702a connecting the instrumentation to analysing equipment (not shown).

FIG. 7 illustrates how (in similar fashion to FIG. 6) the double particle velocity $2U_{sy}$ can be measured for a shear wave, propagating in a direction normal to the free surface. $C_{sx}$ and $U_{sy}$ means respectively the velocity of a shear wave in the x direction and $U_{sy}$ means a corresponding particle velocity perpendicular to the front of the shear wave; the capability of measuring $U_{sy}$ is given by the orientation at 90° with respect to the rod axis, of the strain gauge 602a. However, a shear wave propagating along the free surface $r_1$ where a gauge 700 is glued will cause movement of the free surface with the particle velocity $U_{sx}$. Rod gauge 700 can be employed to measure this value (not doubled) by strain gauge 702 in FIG. 8. Of course, the three rod gauges 500,600 and 700 could be replaced by a single rod gauge instrumented with the instrumentation 502,602,702 to measure all three parameters discussed in relation to FIGS. 6,7 and 8.

The measuring instrumentation on the rod gauge may thus include a set of electrical resistance strain gauges glued on the rod in different directions to allow division of information into intensities of longitudinal and shear components of arrived pertubation. A measuring instrument oriented along the rod will provide information regarding amplitude and impulse duration of a longitudinal wave. A pair of gauges arranged at two diametrically opposed positions oriented perpendicular to the longitudinal axis of the rod will provide information regarding the amplitude of shear waves with corresponding directions of particle velocity. $U_{sy}$ indicates particle velocity in a shear wave with direction being perpendicular to the velocity of shear wave propagation.

Figure 9:
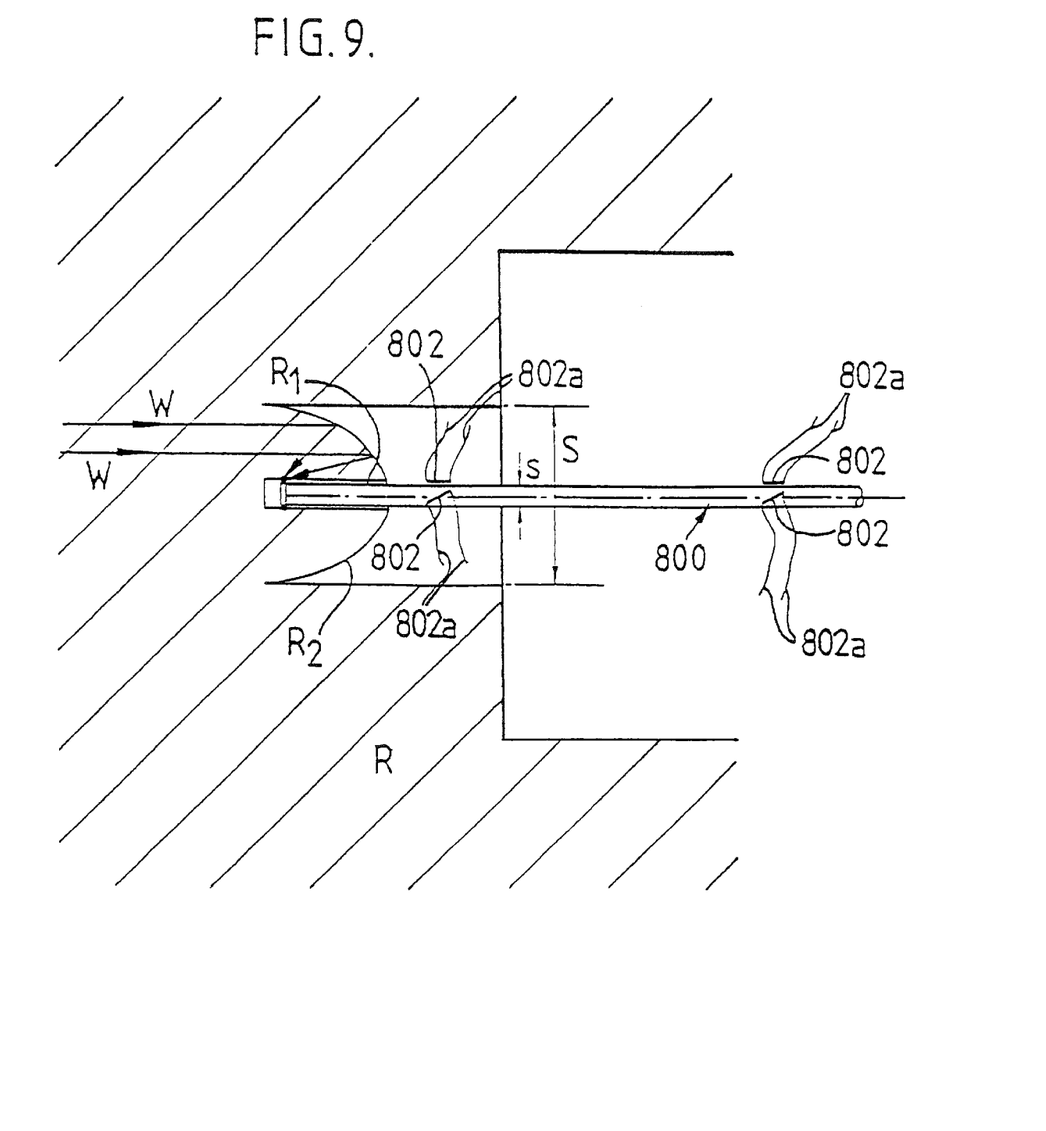
FIG. 9 shows a rod measuring gauge in accordance with the present invention in combination with a wave reflecting system.

In order to increase the sensitivity of the measuring gauge for wave analysis in geological structures, for example in order to receive reliable information about rupture development either in a possible future epicentre of a strong earthquake or in a centre of energy accumulation so rock massive of a mine with a complex geological structure inclined to a rock impact formation, the arrangement shown in FIG. 9 could be adopted. A distance from the rod gauge 800 to a probable crack may be about 50 to 100 km, in the case of an earthquake epicentre or about 1 to 5 km in the case of stress redistribution in a mine due to removal of some volumes of ore and industrial explosions. The amplitude of expected signals is in proportional to the distance. Thus, an amplitude can be very small, at the level of a background noise fixed by standard earthquake gauges and therefore the sensitivity of the measuring apparatus device may need to be higher than that provided for in FIGS. 6 to 8. In order to increase the sensitivity of the apparatus, for example, as shown in FIG. 9 an analogy is adopted between optical waves and sound waves. For example, the amplitude of a signal may be increased essentially by a reflecting system (FIG. 9) or a refracting system (SEE FIGS. 10 and 11). With reference to FIG. 9, by the flux conservation law, the particle velocity of a signal at focal plane could be estimated as $U=U_O S/s$ where $U_O$ is a particle velocity in a falling wave at the entrance section S and s is the section of "an image" that is a cross section of the rod gauge where a signal U is measured.

FIG. 9 shows a rock massive R cut to a shape shown in the FIGURE with the rod gauge 800 inserted into a tubular hole $R_1$, arranged centrally of a parabolic shaped rock surface $R_2$. A reflecting system with a parabolic surface $R_2$ is easier to fabricate than a refracting system but an analysis of the measured signal from the instrumentation gauges 802 (having leads 802a to analysing equipment—not shown) will be more complicated due to the splitting of the falling longitudinal wave at the reflection from the inclined surface for longitudinal and shear waves. As should be evident from FIG. 3, waves W travelling in the rock massive R are reflected by the paraboloid surface $R_2$ onto the rod gauge 800, the reflection and the successive focussing effect thus amplifying the signal.

Figure 10:
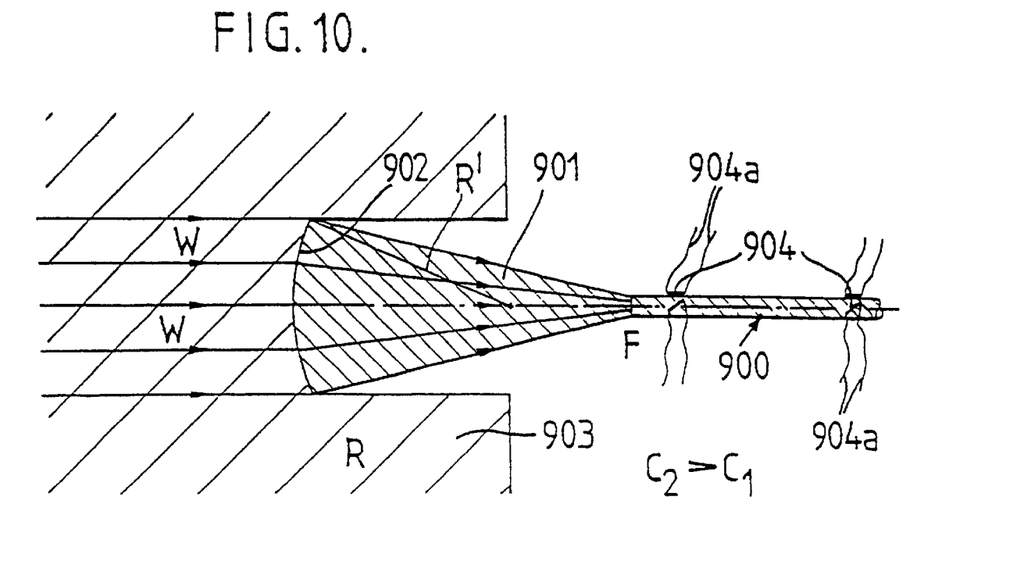
FIG. 10 shows a rod measuring gauge in accordance with the present invention in combination with a wave refracting system.
Figure 11:
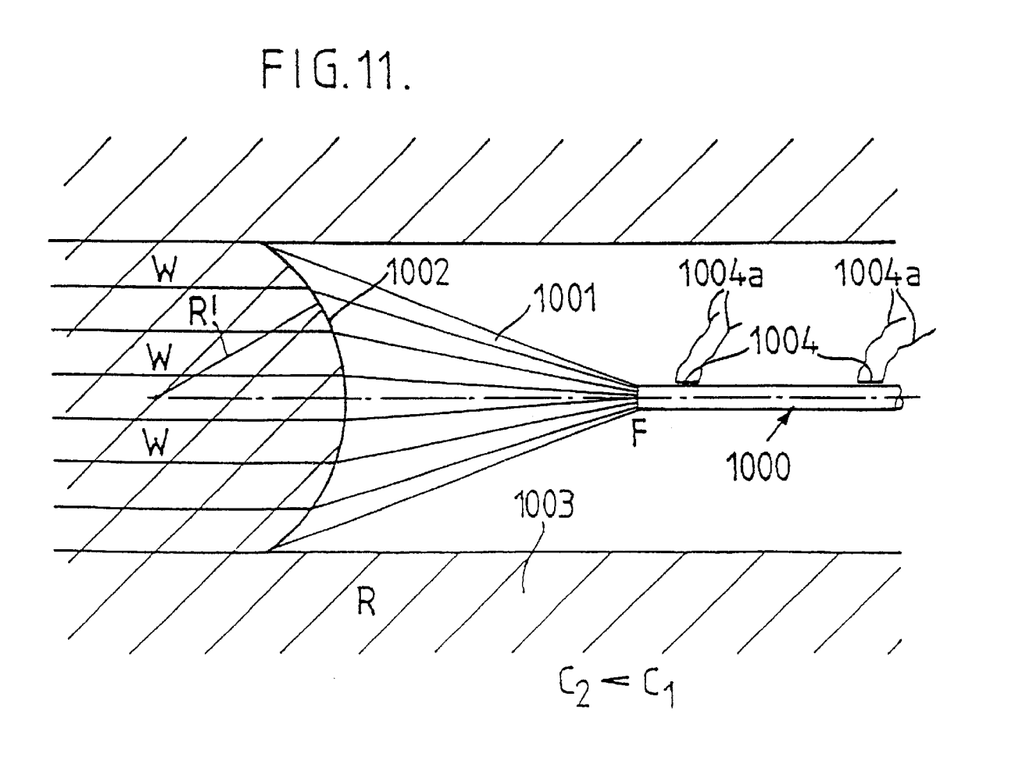
FIG. 11 shows an arrangement similar to FIG. 10 but modified to take into account the relation between the sound velocity values in rock massive material under test and an attached rod cone.

FIGS. 10 and 11 show alternative arrangements X,Y for measuring signals amplified by refracting systems.

In FIGS. 10 and 11 a cone of material 901,1001, is positioned in between one end of the rod gauge 900,1000 and a concave rock massive surface 902 of rock massive 903 (FIG. 10) or a convex rock massive surface 1002 of rock massive 1003. The use of a particular one of the two arrangements X,Y shown in FIGS. 100and 11 will depend on the relationship between the sound wave velocities $C_1,C_2$ in the rock massive material and in the material of the respective cone 901,1001 extending in between the concave or convex surface 902,1002 and the end of the rod 900 or 1000.

The focal distance of a spherical surface 902,1002 (spherical in approximation of small angles) is $$F=R'C_1/(C_2-C_1).$$

Thus, the arrangement shown in FIG. 10 represents the situation where the velocity of wave $C_1$ in the rock material is less than the velocity of the wave $C_2$ in the material cone 901. R' is the radius of the spherical surface.

However, when the velocity of sound wave is greater in the rock material than in the material cone (i.e. $C_1$ is greater than $C_2$) the arrangement shown in FIG. 11 needs to be adopted. Thus, when $C_2$ is greater than $C_1$ a concave rock surface 902 mating with a convex cone surface is required as in FIG. 10. When $C_2$ is less than $C_1$ a convex rock surface 1002 is required to mate with a convex cone surface shown in FIG. 11.

In each case, the waves W in the rock massive 903,1003 will be amplified when refracted in the cone material 901, 902 thus transmitting amplified signals to the rod gauge 900,1000 equipped with instrumentation 904,1004 with leads 904a,1004a to analysing equipment (not shown).

The material cone 901,1001 may comprise a liquid as the refracting material inside a thin walled rubber or plastic envelope or the like. Such a scenario facilitates good transmission contact at the convex or concave transmission surface 902,901a;1002,1001a and use of the liquid may allow transmission of virtually only the longitudinal wave in order to measure accurately the given component of a normal stress.

Three normally positioned gauges may be required to give total information about a stress state, created by a wave loading, in a point under investigation. It is possible to avoid practically a reflected signal from the far end of a rather short measuring rod if the liquid is used with an appropriate absorption coefficient.

Overall, therefore, referring to FIGS. 9 to 11, the measuring instrumentation on the rod gauges 900,1000 will measure an amplitude magnified compared with the value of the particle velocity in the falling wave (this signal can be recalculated into displacement and pressure, which is a product of density and values of the wave propagation and particle velocities). Even in the case of pure longitudinally falling waves, after reflection from the inclined surface (see FIG. 9) or refraction at the inclined boundary (see FIGS. 10 and 11) a splitting into two waves occurs (due to inclined direction of a displacement), longitudinal and shear waves travelling with their own velocities. Thus, the correct restoration of the amplitude of a falling wave from the received signal will demand accurate mathematical analysis (it is possible to solve this problem for a fixed geometry and known wave velocities). In order to avoid these complications in analysis in FIGS. 10 and 11, the second refracting medium may be a liquid as previously explained. Shear waves in liquids decay very quickly, thus allowing accurate measurements of the amplitude of longitudinal waves in the rock massive.

When some rupture processes happen in an active zone of rock massive, waves will be generated. Amplitude of fixed signals in three sufficiently remote gauges together with measured delay times permit a finding of the location of the source and an estimate of the intensity of the rupture. Investigation of the history of the rupture process in the zone under study is a fundamental scientific way for dangerous rock impacts and earthquake prediction.

Thus, FIGS. 6 to 11 provide means for recieving, with help stress gauges based on waves mechanics principles, information about crack propagation process in a rock massive which gives a base for an analysis of stress redistribution and energy accumulation in a probable source of a dangerous earthquake or in the probable source of a rock impact.

The above embodiments are described by way of example only. Variations are possible without departing from the invention.

What is claimed is:

1. Apparatus (101) specially designed for measuring mechanical properties or characteristics of a brittle material or structure (102), said apparatus (101) comprising a Hopkinson bar or pressure bar system (103,104) comprising an input bar bundle (103) and an output bar bundle (104), each said bundle comprising a plurality of parallel bars (103a, 104a) each equipped with instrumentation for measuring values of shear wave or shear crack propagation in said brittle material or structure under test located in between said input and output bar bundles (103,104).

2. Apparatus (101) as claimed in claim 1 having means for placing said bar bundles (103,104) and thus the material structure under test in compression in a direction along a longitudinal axis of the bar bundles.

3. Apparatus (101) as claimed in claim 1 or claim 2 in which each bar is equipped with instrumentation (s') to measure the stress-stain relationship in a particular region of the material or structure under test, in addition to measuring values of absorbed energy during rupturing of the material or structure under test, as well as values of shear wave propagation with a known component of compression stress in a crack plane.

4. Apparatus (201) as claimed in any of claims 1 or 2 having means for placing the Hopkinson bar bundles (103, 104) and material structure (101) under test in tension.

5. Apparatus (201) as claimed in claims 1 or 2 in which each bar (203a,204a) is equipped with means for measuring the velocity of a shear crack propagation where the material or structure under test is placed in pure shear.

6. Apparatus as claimed in claim 1 including instrumentation for measuring the following complex of deformation characteristics of brittle materials:

the stress-strain relationship and energy absorption in the material or structure under test during the deformation process; including during the falling part of the load, in conditions of simple stress-state (including tension or compression) and in conditions of complex stress-state (including tension-tension under hydrostatic pressure) and accurate measurements of propagation velocities of both longitudinal and shear waves in such conditions.

7. Apparatus (101) as claimed in any one of claims 1, 2 or 6 in which three measuring gauges are positioned mutually at right angles to one another at a location under investigation.

8. A method of measuring mechanical properties of characteristics of a brittle material or structure (102), said method comprising the steps of: placing a Hopkinson bar or pressure bar system (103,104), including an input bar bundle (103) and an output bar bundle (104), under load, placing said brittle material or structure (102) located in between said input and output bar bundles (103,104), under load, and measuring values of shear wave or shear crack propagation in the brittle material or structure (103,104) from instrumentation provided on a plurality of parallel bars (103a,104a) forming each said bar bundle (103,104).

9. A method as claimed in claim 8 wherein the bar bundles (103,104) and brittle material or structure (102) are placed in compression.

10. A method as claimed in claim 8 wherein the brittle material or structure (202) is placed in "pure shear".

11. A method as claimed in claim 10 wherein the bars (203a,204a) are used as receptors of stress waves.

12. A method as claimed in claim 8 wherein the brittle material or structure (302) is placed under hydrostatic pressure.

13. Measuring apparatus arranged to measure wave effects generated in a geological structure (R), comprising a rod (600) adapted to be fixed to a surface ($r_1$) of said geological structure to receive a longitudinal wave, and wherein said rod (500) is instrumented with sets of gauges (502,602,702) attached to the rod (700) in different directions to allow division of information into intensities of longitudinal and shear components of arrived perturbation, to enable measurement of shear wave or shear crack propagation in said structure.

14. Apparatus (900,1000) as claimed in claim 13 having a refracting amplification system including a generally cone shape of material (901,1001) extending, in use, between one end of the rod (900,1000) and a suitably shaped surface of the structure (R).

15. Apparatus (500,600,700,800,900,1,000) as claimed in either claim 13 or 14 in which three measuring gauges (500,800) are positioned mutually at right angles to one another at a location under investigation.

16. A method of measuring values of shear wave or shear crack propagation in a structure (R) using measuring apparatus (800) comprising a rod (800) instrumented with sets of gauges attached to the rod in different directions arranged to measure wave effects generated in said structure (R).

17. A method as claimed in claim 16 including the step of arranging the rod (800) to receive an amplified signal of wave effects generated in the structure using a reflecting or refracting system.

18. A method as claimed in claim 17 including the step of positioning the rod (800) into a tubular hole (R1) arranged centrally of a convex surface (R2) cut or shaped into the structure (R) under test.

19. A method as claimed in claim 17 including the step of providing a generally cone shape of material (901,1001) and placing this between one end of the rod (900,1000) and a suitably shaped surface of the structure (R).

20. A method as claimed in claim 19 in which the structure surface (902) is concave and the velocity of sound waves ($C_2$) in the cone material (901) is greater than the velocity of sound waves ($C_1$) in the material of the structure (R).

21. A method as claimed in claim 19 in which said structure surface (1002) is convex and the velocity of sound waves ($C_2$) in the cone material (1001) is less than the velocity of sound waves ($C_1$) in the material of the structure (R).

22. A method as claimed in any one of claims 19 to 21 in which the material cone (901,1001) comprises a liquid as a refracting material inside a rubber or plastic envelope, preferably with a thin wall.

* * * * *